(12) United States Patent
Atwater

(10) Patent No.: US 9,662,499 B2
(45) Date of Patent: May 30, 2017

(54) SYSTEMS AND METHODS FOR OPTIMIZING CARDIAC RESYNCHRONIZATION THERAPY (CRT)

(71) Applicant: Duke University, Durham, NC (US)

(72) Inventor: Brett D. Atwater, Durham, NC (US)

(73) Assignees: U.S. Department of Veteran Affairs, Washington, DC (US); Duke University, Durham, NC (US)

( * ) Notice: Subject to any disclaimer, the term of this patent is extended or adjusted under 35 U.S.C. 154(b) by 1 day.

(21) Appl. No.: 14/760,470

(22) PCT Filed: Jan. 20, 2014

(86) PCT No.: PCT/US2014/012185
§ 371 (c)(1),
(2) Date: Jul. 11, 2015

(87) PCT Pub. No.: WO2014/116535
PCT Pub. Date: Jul. 31, 2014

(65) Prior Publication Data
US 2015/0352358 A1    Dec. 10, 2015

Related U.S. Application Data

(60) Provisional application No. 61/755,016, filed on Jan. 22, 2013.

(51) Int. Cl.
*A61N 1/368* (2006.01)
*A61N 1/362* (2006.01)
(Continued)

(52) U.S. Cl.
CPC .......... *A61N 1/3627* (2013.01); *A61B 5/1072* (2013.01); *A61N 1/368* (2013.01); *A61N 1/36578* (2013.01); *A61N 1/36514* (2013.01)

(58) Field of Classification Search
None
See application file for complete search history.

(56) References Cited

U.S. PATENT DOCUMENTS 6,438,408 B1 * 8/2002 Mulligan ........... A61N 1/36564
600/510
8,135,455 B2   3/2012 Holmstrom
(Continued)

OTHER PUBLICATIONS

PCT Search Report and Written Opinion dated May 1, 2014 for PCT International Application No. PCT/US2014/012185.

*Primary Examiner* — Kennedy Schaetzle
(74) *Attorney, Agent, or Firm* — Olive Law Group, PLLC

(57) ABSTRACT

Systems and methods for optimizing CRT are disclosed. According to an aspect, a method includes receiving, during at least two time periods of a cardiac cycle, electrical signals communicated by two or more electrodes of a CRT device positioned one or more of on a surface of a body, within a thorax of the body, a heart of the body, a surrounding venous structure of the body, and a surrounding subcutaneous structure of the body. The method also includes calculating, based on the received electrical signals, spacing between the two or more electrodes during the at least two time periods of the cardiac cycle. Further, the method includes controlling output of the CRT device to the electrodes based on the calculated spacing between the two or more electrodes.

21 Claims, 9 Drawing Sheets

(51) Int. Cl.
*A61N 1/365* (2006.01)
*A61B 5/107* (2006.01)

(56) References Cited

U.S. PATENT DOCUMENTS

| | | |
|---|---|---|
| 2006/0224203 A1 | 10/2006 | Hettrick et al. |
| 2009/0254140 A1 | 10/2009 | Rosenberg et al. |
| 2010/0152801 A1 | 6/2010 | Koh et al. |
| 2011/0092809 A1 | 4/2011 | Nguyen et al. |

\* cited by examiner

SYSTEMS AND METHODS FOR OPTIMIZING CARDIAC RESYNCHRONIZATION THERAPY (CRT)

CROSS REFERENCE TO RELATED APPLICATIONS

This application is a 35 U.S.C. 371 application of PCT International Patent Application Number PCT/US2014/012185, filed Jan. 20, 2014, which claims the benefit of U.S. Provisional Patent Application No. 61/755,016, filed Jan. 22, 2013; the disclosures of which are incorporated herein by reference in their entireties.

BACKGROUND

Heart failure (HF) currently affects about 5.2 million Americans (2.5% of the total U.S. population) with 550,000 new cases diagnosed each year (see, e.g., Aranda, J. M. et al. (2004) Clin. Cardiol. 27:678-682; Lloyd-Jones, D. et al. (2009) Circulation 27:119:480-486). The estimated annual cost of HF in the United States in 2007 was $33.2 billion, more than any other medical diagnosis (see, e.g., Lloyd-Jones, D. et al. (2009) supra). The cost was driven largely by frequent hospital admissions for poorly controlled symptoms. Among patients over age 65, HF is the leading cause of hospitalization, followed by pneumonia, cerebrovascular disease, cancer, and coronary atherosclerosis (see, e.g., Rosamond, W. et al. (2007) Circulation 115:e69-171). An urgency to improve our understanding of HF and to develop new treatment modalities results from the rapidly rising incidence of HF. The number of hospitalizations in the United States with any mention of HF tripled from 1,274,000 in 1979 to 3,860,000 in 2004 (see, e.g., Kozak, L. I. et al. (2006) Vital Health Stat. 160:1-206). Cardiac dyssynchrony is present in the majority of patients with HF and usually manifests as prolongation of the QRS interval on surface electrocardiogram. Cardiac Resynchronization Therapy (CRT) can restore synchronous LV contraction in some patients with dyssynchrony.

Numerous randomized controlled trials have demonstrated significant reduction in all-cause mortality, cardiovascular mortality, HF hospitalizations, and LV size and improvements in quality of life, 6-minute walk distance, and left ventricular ejection fraction with CRT compared to placebo (see, e.g., Cleland, J. G. F. et al. (2005) N. Eng. J. Med. 352:1539-1549; Higgins, S. L. et al. (2003) J. Am. Coll. Cardiol. 42:1454-1459; Abraham, W. T. et al. (2004) Circulation 110:2864-2868; Linde, C. et al. (2008) J. Am. Coll. Cardiol. 52:1834-1843; Moss, A. J. et al. (2009) N. Eng. J. Med. 361:1329-1338; Tang, A. S. et al. (2010) N. Eng. J. Med. 363:2385-2395). Cost-effectiveness analyses have shown CRT to be attractive when used in patients meeting current ACC/AHA guideline indications (see, e.g., Linde, C. et al. (2011) Eur. Heart J. 32:1631-1639).

Although CRT results in reductions in important endpoints in the majority of patients who meet therapeutic criteria, a large minority of patients (30-40%) obtain no benefit (see, e.g., Lindenfeld, J. et al. (2007) Circulation 115:204-212). Improving response in this group has the capacity to improve both the risk/benefit ratio and cost-effectiveness of the procedure. Previous work has identified several patient and procedural characteristics associated with lower CRT response rate. Patients with QRS duration between 120 msec and 150 msec do not appear to benefit as much as patients with QRS duration >150 msec (see, e.g., Daubert, C. et al. (2009) J. Am. Coll. Cardiol. 54:1837-1846). Patients with right bundle-branch block or non-specific interventricular conduction delay do not benefit as much as patients with left bundle-branch block and patients with apical left ventricular lead placement do not benefit as much as patients with more basal/lateral left ventricular lead placements (see, e.g., Zareba, W. et al. (2011) Circulation 123:1061-1072; Singh, J. P. et al. (2011) Circulation 123:1159-1166). Other predictors of response to CRT therapy are the physical separation of the left and right ventricular lead tips, gender, and type of HF (e.g., ischemic v. non-ischemic etiology).

Hence, there is a need for optimization of current CRT therapy to better improve the risk-benefit ratio and cost-effectiveness of the procedure.

BRIEF SUMMARY

Disclosed herein are systems and methods for optimizing CRT. According to an aspect, a method includes receiving, during at least two time periods of a cardiac cycle, electrical signals communicated by two or more electrodes of a CRT device positioned one or more of on a surface of a body, within a thorax of the body, a heart of the body, a surrounding venous structure of the body, and a surrounding subcutaneous structure of the body. The method also includes calculating, based on the received electrical signals, spacing between the two or more electrodes during the at least two time periods of the cardiac cycle. Further, the method includes controlling output of the CRT device to the electrodes based on the calculated spacing between the two or more electrodes.

According to another aspect, a CRT system includes multiple electrodes including two or more electrodes positioned one or more of on a surface of a body, within a thorax of the body, a heart of the body, a surrounding venous structure of the body, and a surrounding subcutaneous structure of the body. The CRT system also includes a CRT device configured to receive, during at least two time periods of a cardiac cycle, electrical signals communicated by the two or more electrodes. Further, the CRT device is configured to calculate, based on the received electrical signals, spacing between the two or more electrodes during the at least two time periods of the cardiac cycle. The CRT device is also configured to control output of electrical signals to the electrodes based on the calculated spacing between the two or more electrodes.

BRIEF DESCRIPTION OF THE SEVERAL VIEWS OF THE DRAWINGS

The foregoing aspects and other features of the present subject matter are explained in the following description, taken in connection with the accompanying drawings, wherein.

DETAILED DESCRIPTION

Figure 1:
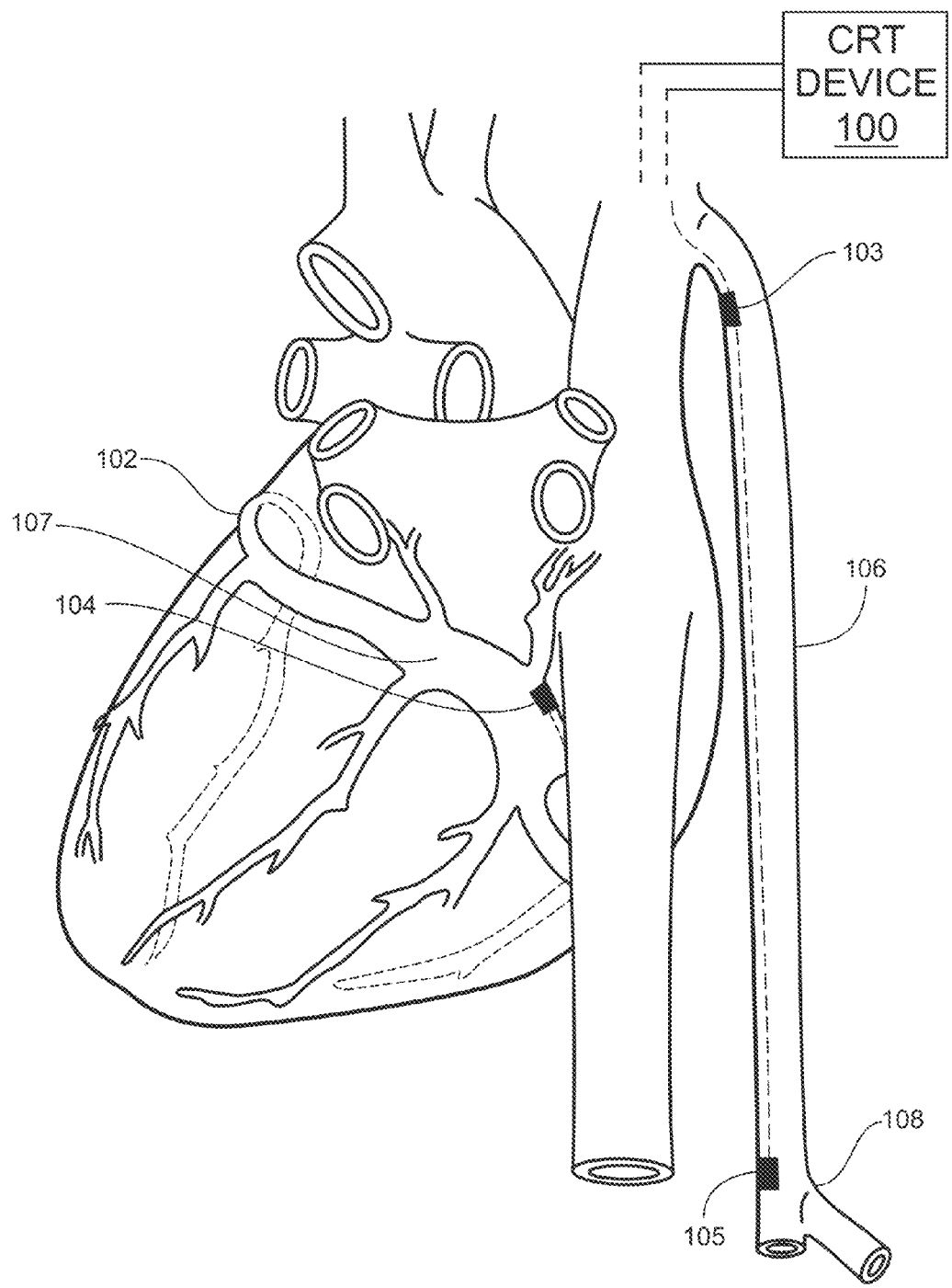
FIG. 1 is a diagram of an exemplary system including a CRT device in electrical communication with a patient's heart by way of three reference leads comprising one or more electrodes positioned posterior to the left ventricle suitable for delivering multi-chamber stimulation and shock therapy in accordance with embodiments of the present disclosure.

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

As used herein, the terms "patient" and "subject" are used interchangeably and are intended to include human and non-human animals. Exemplary human subjects include a human patient in need of CRT, for example, patients having suffered a myocardial infarction, heart attack, and the like. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, and the like), and rodents (such as mice, rats, hamsters, guinea pigs, and the like).

Various exemplary methods, devices, systems and the like provided herein may rely on data (e.g., electrical, ultrasound, magnetic signals, etc.) collected from a plurality of electrodes positioned within a subject to: (a) optimize CRT; (b) to monitor a patient's condition, including but not limited to, heart failure monitoring; (c) to provide assessment of dynamic changes in cardiac contractility associated with stress or exercise as a means to provide rate adaptive pacing; (d) to provide assessment of dynamic changes in cardiac contractility associated with cardiac arrhythmias as a means to distinguish hemodynamically stable and hemodynamically unstable tacharrhythmias; (e) to monitor implantable device condition; and/or (f) to more fully understand cardiac health.

As used herein, the term "data" may include, but is not limited to, any mechanical, electrical, ultrasound, magnetic signals, radiofrequency, the like, and combinations thereof that may be detected by the electrodes.

As used herein, the term "electrode" may refer to an electrical conductor used to make contact with a non-metallic component for sensing or detecting electrical signals. For example, electrodes disclosed herein may be positioned within veins or an organ (e.g., the heart) for sensing electrical signals. An electrode may be in electrical communication (e.g., via a wire) with a CRT device for communication of the sensed electrical signal to the CRT device.

As described herein, the systems and methods may comprise, consist of, or consist essentially of one or more pairs of reference electrodes and one or more pairs of pacing electrodes in electrical communication with a CRT device. The reference and pacing/sensing electrodes are configured to deliver and sense, respectively, small electrical, mechanical, ultrasound or magnetic signals delivered by the CRT device through the subject's body. In certain embodiments, the electrodes are implantable. Such electrodes may be unipolar or bipolar, and may be made of any suitable conducting material, such as, for example, stainless steel, ELGILOY® (a Co—Cr—Ni alloy), or MP35N alloy. The electrodes may be insulated with materials such as silicone rubber, polyurethane, or the like. In yet other embodiments, the reference electrodes may be placed on the body surface (e.g., such as a patch attached to a patient's chest or back). Such suitable reference electrodes include, but are not limited to, existing ENSITE/NAVX™ patches. These electrodes may be attached to leads (e.g., a lead may comprise one or more electrodes). The leads may be operatively connected to a CRT device, or function as independent satellite devices that are capable of communicating wirelessly (e.g., BLUETOOTH® wireless technology, WI-FI® wireless technology, or the like) with the CRT device.

Position tracking of the electrodes may be achieved in any of a variety of suitable manners to define a coordinate system (e.g., three-dimensional (3D) coordinate system) and to aid in acquisition of position and motion information for one or more implanted electrodes (e.g., due to cardiac mechanics). An implanted electrode may be positioned via a vessel (e.g., a vein) or via the pericardium (e.g., intrapericardial access to an epicardial location).

In other embodiments, the electrical information may be acquired as well and optionally used for gating acquisition of mechanical information or other purposes. Electrical activity may be measured using conventional techniques such as those for acquiring surface electrocardiograms or in vivo electrocardiograms. As described herein, the term "electrocardiogram" (EGM) includes surface electrocardiogram (ECG) and intracardiac electrogram (IEGM) as well as other types of electrograms that rely on one or more implanted electrodes.

Data that is collected may be analyzed with respect to stimulation energy delivered using one or more stimulation sites and/or one or more A-V intervals or V-V intervals. An analysis of such information may be used to determine an optimal pacing configuration. As used herein, the term "configuration" can account for more than electrode placement or location as one or more stimulation parameters and/or stimulation timings (e.g., interelectrode or intraelectrode timings) may be part of a "configuration."

An exemplary CRT device, also referred to herein as a "stimulation device," is described followed by various techniques for positioning the electrodes as well as acquiring and analyzing the data collected. In certain embodiments, the CRT device may comprise, consist of, or consist essentially of hardware, software, firmware, or combinations thereof configured to perform post-processing of information (e.g., mechanical, electrical, ultrasound, magnetic signals, or the like) and be configured for programming or operating an implantable device capable of delivering CRT.

An exemplary method (and system for carrying out the method) includes using 3D electrode positioning and motion analysis performed by a CRT pulse generator and multiple reference and pacing electrodes positioned in and around a patient's heart. Further, the exemplary method may include acquiring data (e.g., mechanical position information) during at least part of a cardiac cycle for the chronic monitoring (e.g., throughout the life of the CRT pulse generator) of mechanical motion recorded by the electrodes, thereby facilitating the ongoing real-time analysis of cardiac wall motion.

Exemplary positions of the electrodes are provided below and are meant to be illustrative in nature only. It is recognized that one skilled in the art may make changes and/or modifications to the number of, or placement of such electrodes to achieve similar results. Such changes and/or modifications are within the scope of the present disclosure.

FIG. 1 illustrates a diagram of an exemplary system including a CRT device 100 in electrical communication with a patient's heart 102 by way of three reference leads 103, 104, and 105 comprising one or more electrodes positioned posterior to the left ventricle suitable for delivering multi-chamber stimulation and shock therapy. In such a configuration, the electrodes are positioned widely within the venous vasculature. In accordance with embodiments, and as shown in FIG. 1, a first electrode 103 is positioned in the proximal azygos vein 106, a second electrode 104 is positioned in the proximal coronary sinus 107, and a third electrode 105 is positioned at or near the bifurcation of the azygos and hemiazygos vein 108.

Figure 2:
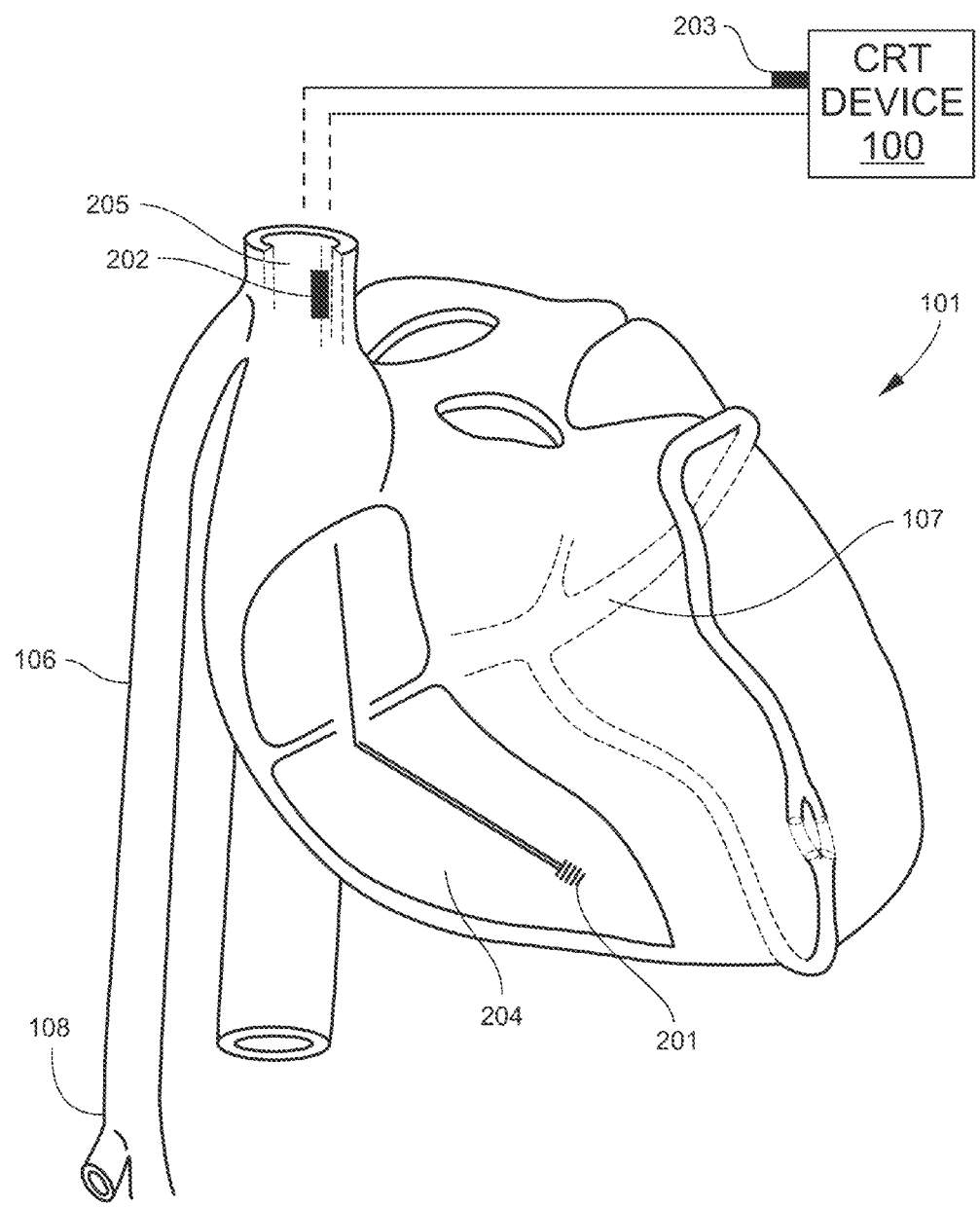
FIG. 2 is a diagram of an exemplary system including three anterior reference electrodes comprising one or more electrodes which are positioned in the right ventricle, the superior vena cava, and at or near the CRT device suitable for delivering multi-chamber stimulation and shock therapy in accordance with embodiments of the present disclosure.

FIG. 2 illustrates a diagram of an exemplary system including three anterior reference electrodes 201, 202, and 203 comprising one or more electrodes which are positioned in the right ventricle 204, the superior vena cava 205, and at or near the CRT device 100, respectively, suitable for delivering multi-chamber stimulation and shock therapy in accordance with embodiments of the present disclosure. In some embodiments, the anterior electrodes may include right ventricle and superior vena cava shocking coils and the CRT case. In other embodiments, other electrodes may be positioned on or attached to these leads to provide the same or improved reference locations.

Figure 3:
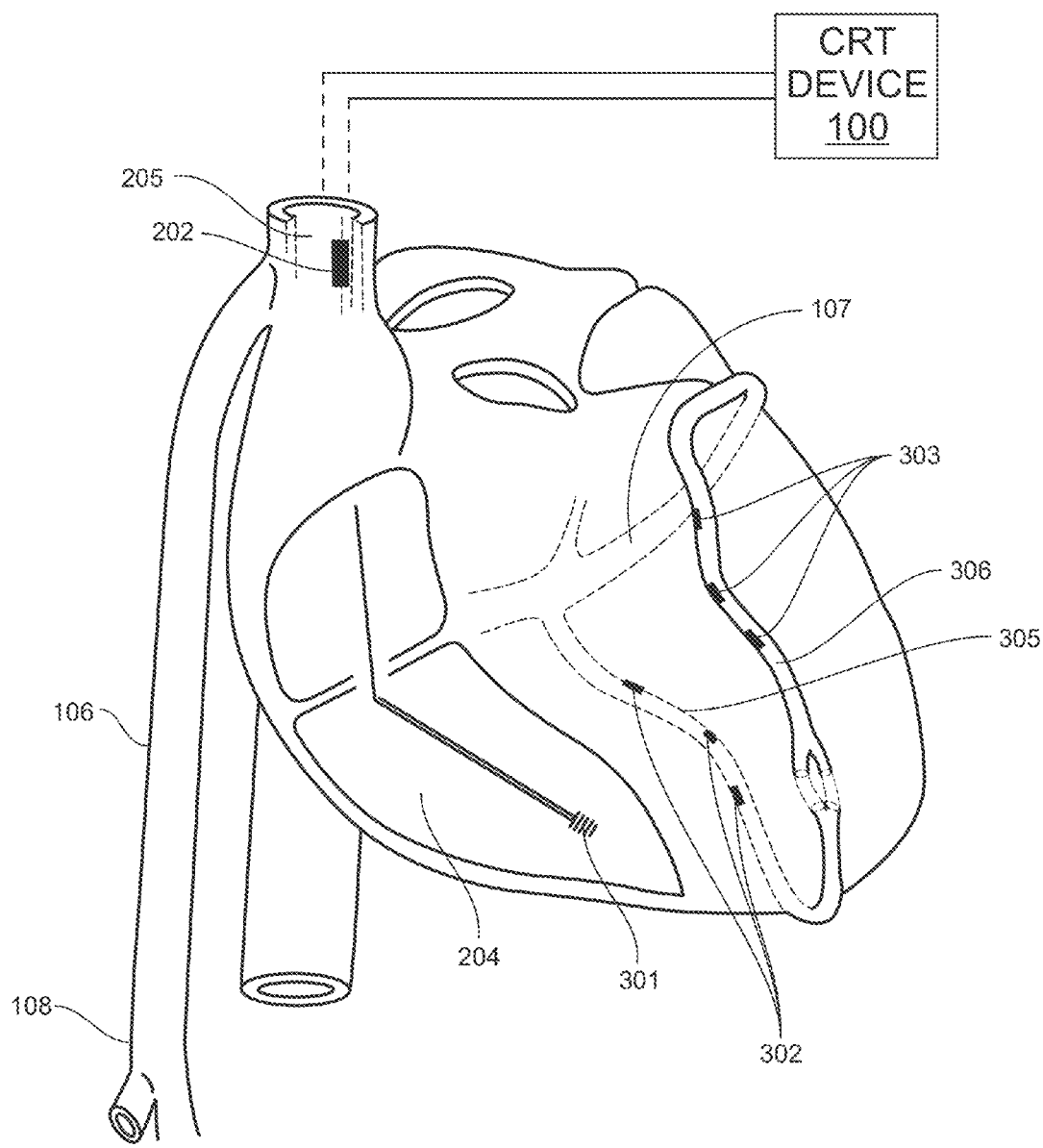
FIG. 3 is a diagram showing exemplary positions of pacing/sensing leads including electrodes within a heart suitable for delivering multi-chamber stimulation and shock therapy in accordance with embodiments of the present disclosure.

A number of different pacing/sensing electrode configurations are also contemplated for use with the systems and methods of the present disclosure. For example, one or more pacing electrodes may be placed in the right ventricle along the intraventricular septum or apex and one or more pacing electrodes may be placed along the endocardial or epicardial surface of the left ventricle. The more pacing/sensing electrodes that are available for motion analysis, the more accurate the system can be able to assess left ventricular volumes and ejection fractions. In accordance with embodiments of the present subject matter, FIG. 3 illustrates a diagram showing exemplary positions of pacing/sensing leads including electrodes within a heart suitable for delivering multi-chamber stimulation and shock therapy in accordance with embodiments of the present disclosure. In such a configuration, a lead (e.g., a bipolar lead) 301 can be positioned in the right ventricle 204. In accordance with embodiments, the lead 301 may be attached to the interventricular septum (not shown). A second lead 302 including one or more electrodes may be positioned through the coronary sinus to the posterior or lateral branch 305. A third lead 303 including one or more electrodes can be positioned through the coronary sinus to either a lateral or anterior branch 306. An unlimited number of total electrodes can be used and positioned along the septal, anterior, and lateral left ventricular walls to allow mapping and visualization along the base, mid, and/or apical areas by the systems and methods described herein. The leads 103, 104, 105, 201, 202, 203, 301, 302, and 303 may be configurable for delivery of stimulation pulses suitable for stimulation of nerves or other tissue. Such leads may also include features such as bifurcations or legs. For example, a pacing lead as disclosed herein may include electrodes capable of delivering pacing pulses to a patient's left ventricle and one or more electrodes capable of stimulating an autonomic nerve. The same reference electrodes may also be used for high voltage defibrillation, pacing, or sensing of intrinsic cardiac signals. For example, the reference electrodes positioned in the azygos vein may be suitable to function as either the cathode or anode for defibrillation energy delivery. Further, the electrodes positioned in the proximal coronary sinus may function as an atrial pace/sensing electrode to time ventricular pacing.

Figure 4:
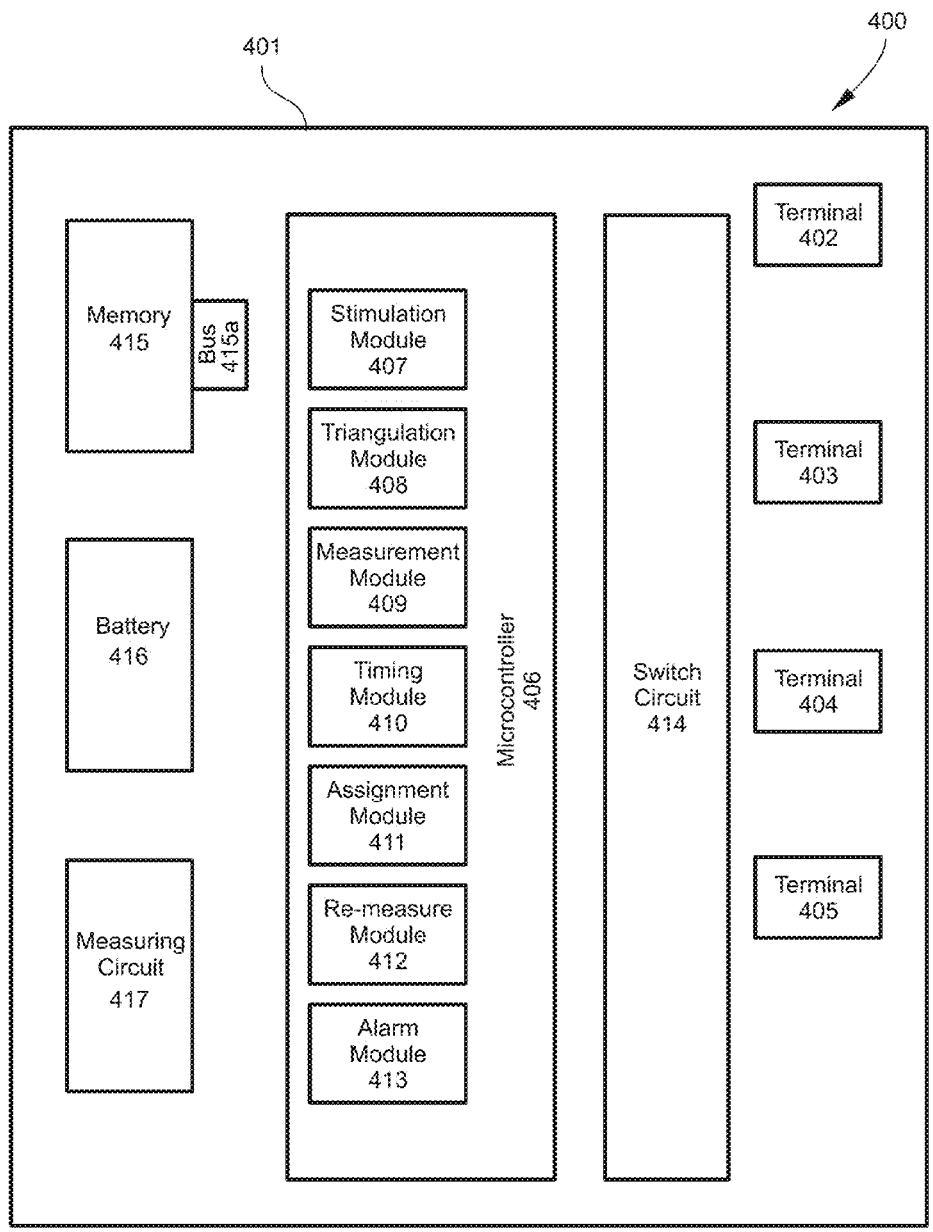
FIG. 4 is a block diagram showing various example components of a CRT device in accordance with embodiments of the present disclosure.

FIG. 4 illustrates a block diagram depicting various example components of a CRT device 400 in accordance with embodiments of the present disclosure. While the diagram shown depicts a multi-chamber device, it is to be understood and appreciated that this is done for illustrative purposes only. Thus, the techniques, methods, and other examples described herein can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

A housing 401 for the CRT device 400 is often referred to as the "can," "case" or "case electrode," and may be programmably selected to act as the return electrode for all "unipolar" modes. The housing 401 may further be used as a return electrode alone or in combination with one or more of the coil electrodes for shocking or other purposes. The housing 401 may include a connector having a plurality of terminals 402, 403, 404, and 405 that are configured to connect the reference and/or pacing/sensing leads (shown schematically, the number of connectors provided here is for illustrative purposes only). It is noted that one or more of the components of the CRT device 400 or any CRT device include the functionality described herein may be implemented by hardware, software, firmware, or combinations thereof The stimulation device 400 is a programmable microcontroller 406 that controls the various modes of cardiac or other therapy. As is well known in the art, a microcontroller 406 typically includes a microprocessor, or equivalent control circuitry, designed specifically for controlling the delivery of stimulation therapy and monitoring/processing of mechanical information collected, and may further include RAM or ROM memory, logic and timing circuitry, state machine circuitry, and I/O circuitry. The microcontroller 406 can be configured to process or monitor input signals (data or information) as controlled by a program code stored in a designated block of memory. The type of microcontroller is not critical to the described implementations. Rather, any suitable microcontroller 406 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their interrelationship, see U.S. Pat. No. 4,788,980, also incorporated herein by reference.

In addition to performing the traditional functions of a CRT device, the CRT device 400 can be capable of functioning as a traditional CRT pacemaker/defibrillator to treat both slow and fast arrhythmias with stimulation therapy, including but not limited to, cardioversion, defibrillation, and pacing stimulation 407. The microprocessor 406 may include a triangulation module 408 configured to triangulate positions of the pace-sensing electrodes. For example, the triangulation module 408 may be configured to communicate or otherwise send low amplitude electrical energy through the leads to triangulate the pacing lead positions. The microprocessor 406 may include a measurement module 409 configured to automatically measure the maximum and minimum ventricular volumes extrapolated from the measured electrode positions averaged over several cardiac cycles.

The microprocessor 406 may include a timing module 410 configured to control the timing of the stimulation pulses (e.g., pacing rate, atrio-ventricular (AV) delay, interatrial conduction (AA) delay, or interventricular conduction (VV) delay, pacing electrodes used for ventricular stimulation, and sequence of pacing electrode stimulation). Further, the timing module 410 can keep track of the timing of refractory periods, blanking intervals, noise detection windows, evoked response windows, alert intervals, marker channel timing, and the like. The timing module 410 may be configured to measure the maximum and minimum ventricular volumes extrapolated from the measured electrode positions averaged over several cardiac cycles in each pacing configuration.

The microprocessor 406 may include an assignment module 411 configured to automatically assign permanent pacing programming to the pacing configuration that maximizes the difference in maximum and minimum intra-electrode area or volume (a surrogate marker of stroke volume).

The microprocessor 406 may include a re-measure module 412 configured to re-measure the maximum and minimum intra-electrode area or volume (e.g., stroke volume) over several cardiac cycles in each pacing configuration in various physiological states (e.g., rest, mild exercise, peak exercise, or the like) to determine optimal pacing configurations for each physiological state. The CRT device 400 can subsequently re-measure the maximum and minimum intra-electrode area or volume over several cardiac cycles on a routine bases. Reduction in variation in intra-electrode area or volume (stroke volume) or an increase in overall intra-electrode area or volume (a surrogate measure of LV dilation) can subsequently be used as a marker of worsening heart failure.

The microprocessor 406 may include an alarm module 413 configured to provide an auditory or sensory (e.g., vibration) alert to the patient and/or the medical provider to any worsening heart failure.

The electronic configuration switch 414 may include multiple switches for connecting the desired electrodes to the appropriate I/O circuits, thereby providing complete electrode programmability. Accordingly, the switch 414, in response to a control signal from the microcontroller 406, may determine the polarity of the stimulation pulses (e.g., unipolar, bipolar, or the like) by selectively closing the appropriate combination of switches (not shown) as is known in the art.

The microcontroller 406 may be communicatively connected to a memory 415 by a suitable data/address bus 415a. The programmable operating parameters used by the microcontroller 406 may be stored and modified, as required, in order to customize the operation of the CRT device 400 to suit the needs of a particular patient. Such operating parameters may define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart within each respective tier of therapy. One feature of the described embodiments is the ability to sense and store a relatively large amount of data (e.g., from a data acquisition system). The data may subsequently be used for subsequent analysis to guide the programming of the device.

Advantageously, the operating parameters of the CRT device 400 may be non-invasively programmed into the memory 415 through a telemetry circuit in telemetric communication via communication link with an external device. Exemplary external devices include, but are not limited to, a programmer, transtelephonic transceiver, and a diagnostic system analyzer. The microcontroller 406 may activate the telemetry circuit with a control signal. The telemetry circuit allows intracardiac electrograms (IEGM) and other information (e.g., status information relating to the operation of the device 400 or the like, as contained in the microcontroller 406 or memory 415) to be sent to an external device (not shown) through an established communication link.

The CRT device 400 may include a battery 416 configured to provide operating power to all of the circuits and/or component shown in FIG. 4. For the CRT device 400, which employs shocking therapy, the battery 416 can operate at low current drains for long periods of time (e.g., less than about 10 µA). Further, the battery 416 can provide high-current pulses (for capacitor charging) when the patient requires a shock pulse (e.g., in excess of about 2 A, at voltages above 200 V, for periods of about 10 seconds or more). The battery 416 can have a predictable discharge characteristic so that elective replacement time can be detected.

The CRT device 400 can include magnet detection circuitry (not shown), coupled to the microprocessor 406, and configured to detect when a magnet is placed over the CRT device 400. The magnet may be used by a clinician to perform various test functions of the CRT device 400 and/or to signal the microprocessor 406 that the external programmer is in place to receive or transmit data to the microprocessor 406 through the telemetry circuits.

The CRT device 400 may include an impedance measuring circuit 417 that may be enabled by the microprocessor 406 via a control signal. Example functionality of the impedance measuring circuit 417 includes, but is not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, and the like. The impedance measuring circuit 417 may be coupled to the switch 414 so that any desired electrode may be used.

It is also within the scope of the present disclosure that the CRT device 400 may include one or more physiologic sensors (not shown). For example, the CRT device 400 may include a "rate-responsive" sensor that may provide, for example, information to aid in adjustment of pacing stimulation rate according to the state of the patient, such as diurnal changes in activity (e.g., detecting sleep and wake states). Accordingly, the microcontroller 406 may respond by adjusting the various pacing parameters (such as rate, A-V Delay, V-V Delay, etc.) at which stimulated pulses are generated.

It is to be understood that one or more physiologic sensors may also be external to the CRT device 400, yet still be implanted within or carried by the patient. Examples of physiologic sensors that may be implemented in the CRT device 400 include any suitable sensors that, for example, sense respiration rate, pH of blood, ventricular gradient, cardiac output, preload, afterload, contractility, and the like. Another sensor that may be used is one that detects activity variance, wherein an activity sensor is monitored diurnally to detect the low variance in the measurement corresponding to the sleep state.

The physiological sensor(s) may include sensors for detecting movement and minute ventilation in the patient. Signals generated by a position sensor, e.g., a MV sensor or the like, may be passed to the microprocessor 414 for analysis in determining whether to adjust the pacing rate, and/or the like. The microprocessor 414 may monitor the signals for indications of the patient's position and activity status, such as whether the patient is climbing upstairs or descending downstairs or whether the patient is sitting up after lying down.

The present disclosure further provides an additional module(s) that may be contained within the microprocessor 406 of the CRT device 400 or a CRT device programmer (external to the patient). Such a module(s) may allow for a number of different functions, including but not limited to, the importation of a pre- and/or post-procedurally acquired 3D computed tomography (CT), magnetic resonance image (MRI), echocardiogram, or electroanatomic map images of the left ventricular cavity to be merged with 3D images of the catheter electrode position map to allow the user (e.g., medical professional) to visualize a 3D left ventricular model beating in real-time on an LCD display. Other modules may be configured to display or otherwise present stroke volume and ejection fraction as measured by lead motion.

It is to be understood that the aforementioned components/modules may be implemented in hardware as part of the microprocessor 406, or as software/firmware instructions programmed into the device and executed on the microprocessor 406 during certain modes of operation. Alternatively, additional external devices, such as a CRT device programmer, may be connected to the CRT device to perform one or more of the above-described functions, or additional functions (e.g., provide additional memory/processing functions and the like). Such external devices may be in direct electrical communication or wireless (e.g., BLUETOOTH® wireless technology, WI-FI® wireless technology, or the like) with the implanted CRT device.

Figure 5:
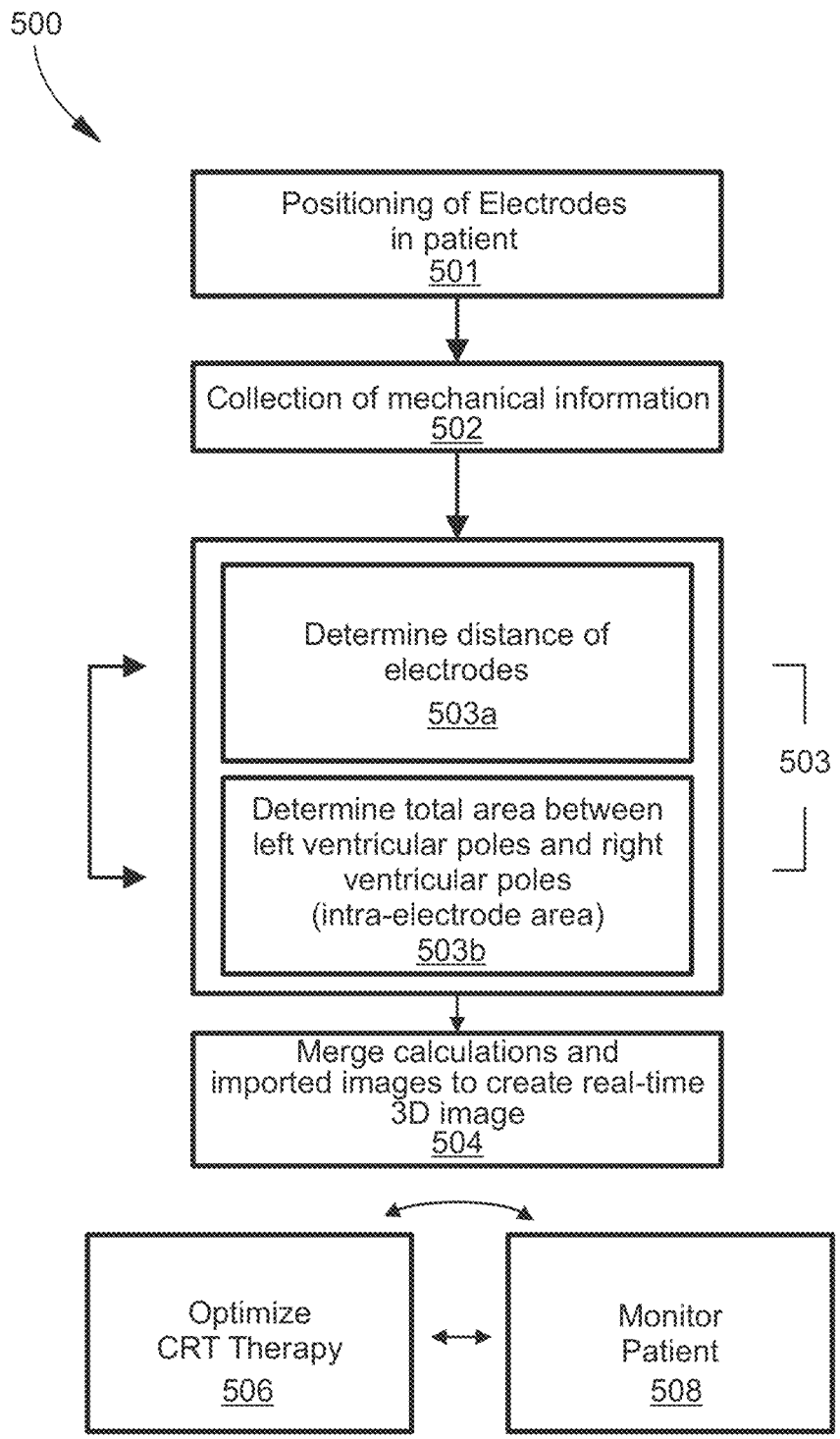
FIG. 5 is a flow chart of an exemplary method for acquiring and analyzing mechanical information in accordance with embodiments of the present disclosure.

FIG. 5 illustrates a flow chart of an exemplary method 500 for acquiring and analyzing mechanical information in accordance with embodiments of the present disclosure. Referring to FIG. 5, the method includes positioning 501 one or more pairs of reference electrodes and one or more pairs of pacing/sensing electrodes in the thorax, heart and/or surrounding venous or subcutaneous structures of the patient (termed "configuration"). The electrodes may be in electrical communication with the CRT device. In embodiments, one or more pairs of reference electrodes may be positioned posterior to the left ventricle, and one or more pairs of reference electrodes may be positioned anterior of the right ventricle. In embodiments, the posterior reference electrodes may be positioned in the proximal azygos vein, the proximal coronary sinus, and at or near the bifurcation of the azygos and hemiazygos vein. In other embodiments, the anteriorly positioned reference electrodes may be positioned in the right ventricle, the superior vena cava, and at or near the CRT device, respectively. In other embodiments, electrodes may be positioned on these leads to provide the same or improved reference locations. In other embodiments, one or more pacing electrodes may be placed in the right ventricle along the intraventricular septum or apex, and one or more pacing electrodes may be placed along the endocardial or epicardial surface of the left ventricle. In embodiments, the one or more pacing electrodes may be positioned in the right ventricle, may be attached to the interventricular septum, one or more electrodes may be positioned through the coronary sinus to the posterior or lateral branch, and one or more electrodes may be positioned through the coronary sinus to either a lateral or anterior branch.

The method 500 of FIG. 5 includes collecting 502 data (e.g., mechanical information) over a period of time (e.g., one or more cardiac cycles). The collected data may be stored in the CRT device. The data may subsequently be processed (block) 503 by the microprocessor within the CRT device. First, the distance between the electrodes for each set of recorded coordinates 503a may be calculated and may be followed by calculating the total area or volume contained between the left and right ventricular poles (termed intra-electrode area or intra-electrode volume) 503b. This process can be repeated over several cardiac cycles. In an exemplary configuration described herein, the CRT device may pass low amplitude current (e.g., ~350 µA at 5.7 kHz) through the chest in three orthogonal (X, Y, and Z) directions between the anterior and posterior electrodes and may measure signal amplitude (V) at each catheter pole. The electrode position may be calculated by dividing each of the 3 amplitudes (V) by the corresponding field strength (V/cm). Other types of electrical, magnetic, radiofrequency, or ultrasound energy may be emitted by the CRT generator or reference electrodes and detected at the pacing electrodes to derive real-time position information. Mechanical LV function can subsequently be assessed by comparing lead motion analyses, and/or variation in intra-electrode area over the cardiac cycle, and/or variation in intra-electrode volume over the cardiac cycle. From this data, the provider can subsequently make adjustments to optimize CRT therapy 506 and/or continue to monitor 508 the patient (e.g., implantation, long-term 3D dimensional lead motion information, and the like). Alternatively, the device can be programmed to automatically adjust pacing parameters (e.g., pacing electrode, A-V timing, V-V timing, or multipolar pacing strategies) to maximize variation in intra-electrode area or volume.

As shown in block 504, the data may subsequently be merged with any pre- and/or post-procedurally acquired 3D computed tomography (CT), magnetic resonance image (MRI), echocardiogram, or electroanatomic map image of the left ventricular cavity to the 3D image of the catheter electrode position map to allow the user to visualize a 3D left ventricular model beating in real-time on an external LCD display.

In other embodiments, information gathered by the systems and methods provided herein relating to a rapid increase in stroke volume (as would be expected in exercise condition) can be used alone or in combination with other sensors (e.g., minute ventilation, lead impedance, and chest wall motion) to adapt atrial and ventricular sequential pacing rate. A rapid reduction in stroke volume, associated with a detected tachyarrhythmia may be used as a tachycardia discriminator to differentiate hemodynamically stable from hemodynamically unstable tachyarrhythmias.

The following examples are offered by way of illustration and not by way of limitation.

EXAMPLES

1. Preliminary Human Study

Introduction: An example method for lead motion analysis has been studied in a total of 3 patients with NYHA class III HF. Patient 1 had baseline right bundle-branch block, while patients 2 and 3 had baseline left bundle-branch block.

Methods: After placing external Ensite-NAVX reference electrodes (St. Jude Medical, Austin Tex.) a Quartet quadripolar left ventricular lead (St. Jude Medical, Minneapolis, Minn.) was positioned in the lateral branch of the coronary sinus, a Durata (St. Jude Medical, Minneapolis, Minn.) bipolar right ventricular lead was positioned in the right ventricular apex, and a Tendril (St. Jude Medical, Minneapolis, Minn.) lead was positioned in the right atrial appendage. The leads were connected to the Ensite-NAVX (St. Jude Medical, Austin, Tex.) mapping system. Pacing was delivered through an external stimulator (Micropace EP Inc., Santa Ana, Calif.). Lead motion analysis was performed during sinus rhythm, pacing from the atrial lead (AAI pacing), pacing from the atrial and right ventricular leads (DDD), pacing from the atrial and left ventricular leads (DDD), and pacing from the atrial lead and both ventricular leads (biventricular pacing, DDD). Analysis was performed after 20 seconds of pacing in each configuration. All DDD pacing utilized an atrioventricular delay of 150 msec. During biventricular pacing the ventricular-ventricular offset was set to 0 msec. In one patient lead motion analysis was repeated during pacing at 85, 100, and 120 beats per minute. Using the Ensite-NAVX system 875 sets of coordinate measurements were made over 8 seconds in each pacing configuration. Coordinates were obtained from all 4 poles of the left ventricular lead, 2 poles on the right ventricular lead, and 2 poles on the right atrial lead. Using Equation 1 the distance between electrodes was calculated for each set of recorded coordinates.

$$\text{Sqrt } ((X1-X2)^2+(Y1-Y2)^2+(Z1-Z2)^2) \quad \text{Equation 1}$$

Figure 6:
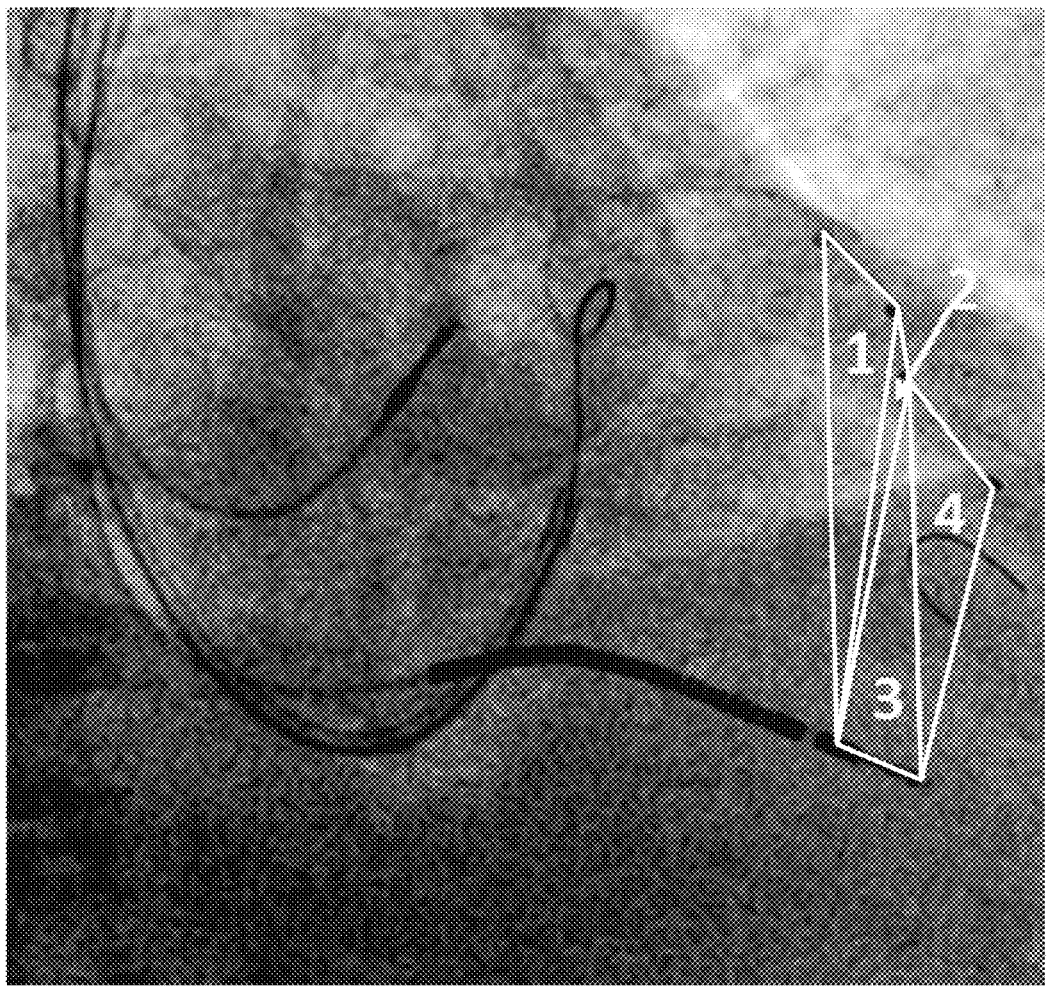
FIG. 6 is an image including a heart with triangles overlaid thereon for calculating the area contained between the left ventricular and right ventricular pacing electrodes in a human subject in accordance with embodiments of the present disclosure.

The total area contained between the 4 left ventricular poles and the 2 right ventricular poles (termed intra-electrode area) was calculated for each set of coordinates by dividing the area into triangles, using Equation 2 to calculate the area of each triangle, and adding the area of all 4 triangles as shown in FIG. 6.

$$\frac{1}{4}*((A^2+B^2+C^2)-2*(A^4+B^4+C^4)) \quad \text{Equation 2}$$

FIG. 6 shows an image including a heart with triangles overlaid thereon for calculating the area contained between the left ventricular and right ventricular pacing electrodes in a human subject in accordance with embodiments of the present disclosure.

The variation in area over several cardiac cycles was computed for each pacing configuration by calculating the difference between the $95^{th}$ percentile (maximum intra-electrode area) and $5^{th}$ percentile (minimum intra-electrode area) intra-electrode area values. Only cardiac cycles acquired at end-expiration were included in intra-electrode area calculations. Differences in intra-electrode area variation were studied using one-way ANOVA tests and two-tailed t-tests. A p-value ≤0.05 was considered significant for all tests.

Results:

A. Comparison of Intra-electrode Area Variation By Pacing Configuration.

Figure 7:
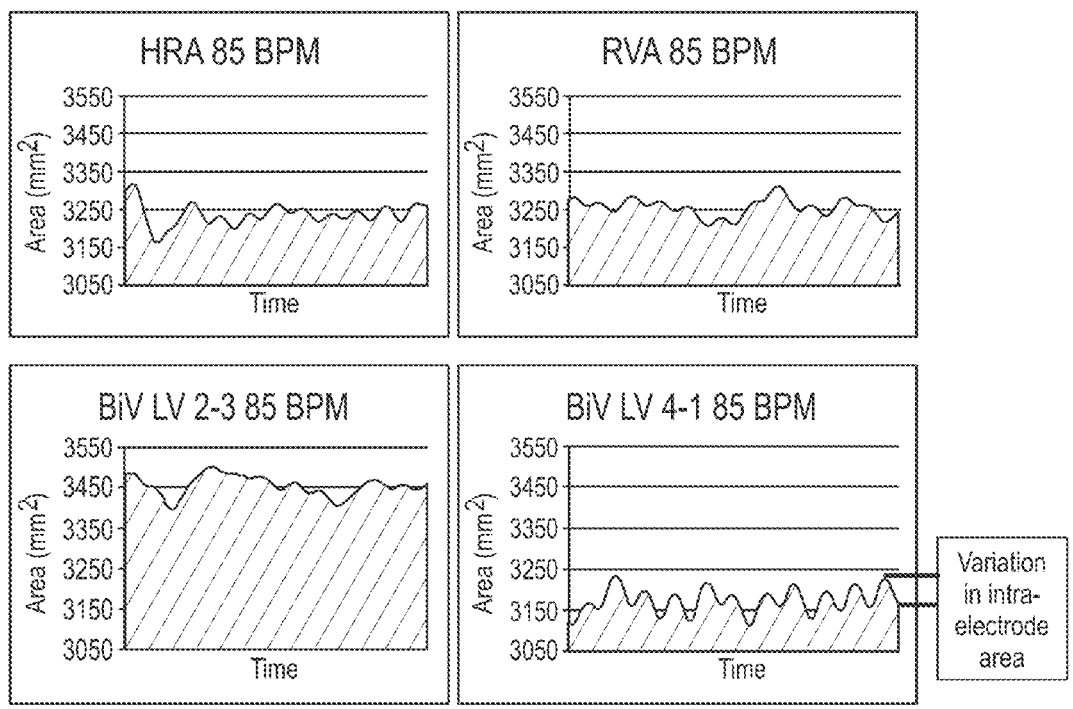
FIG. 7 are graphs showing the raw data for a patient with underlying left bundle-branch block demonstrating intra-electrode area ($mm^2$) on y axis and time (msec) on X axis in accordance with embodiments of the present disclosure.
Figure 8:
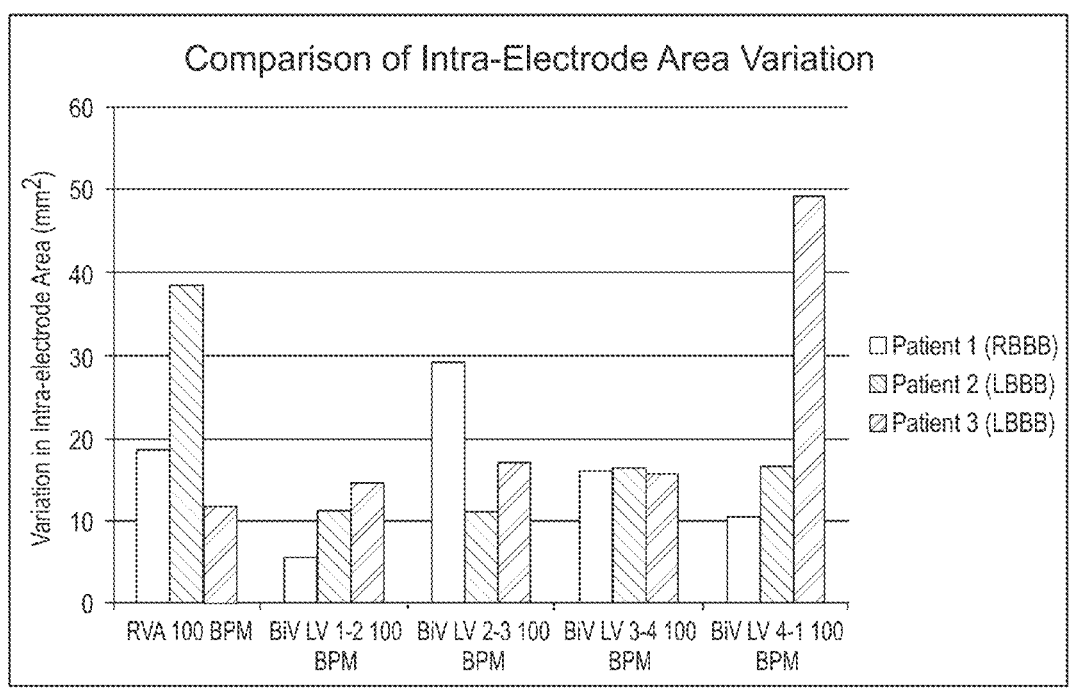
FIG. 8 is a graph showing the comparison of intra-electrode area variation by pacing location among three (3) patient subjects in accordance with one embodiment of the present disclosure.

Intra-electrode area variation over cardiac cycles was measurable using the ENSITE-NAVX system. Raw data (shown in FIG. 7) visually demonstrate differences in intra-electrode area variation based on stimulation site. FIG. 7 are graphs showing the raw data for a patient with underlying left bundle-branch block demonstrating intra-electrode area ($mm^2$) on y axis and time (msec) on X axis in accordance with embodiments of the present disclosure. Formal comparison of intra-electrode area variation is presented in FIG. 8, which shows a graph showing the comparison of intra-electrode area variation by pacing location among three (3) patient subjects in accordance with one embodiment of the present disclosure. Patient 1 (right bundle-branch block) demonstrated maximal variation in intra-electrode area with biventricular pacing with LV stimulation from poles 2-3 (P=3.09 E-29 for comparisons between pacing configurations). Patient 2 (left bundle-branch block) demonstrated maximal variation in intra-electrode area with RV-only pacing (P=2.01E-8 for comparisons between pacing configurations.). Patient 3 (left bundle-branch block) demonstrated maximal variation in intra-electrode area with biventricular pacing with LV stimulation from poles 4-1 (P=1.58 E-21 for comparisons between pacing configurations).

B. Alternative Pacing Strategies To Improve Intra-electrode Area Variation.

LV-only pacing configurations were studied in patient 2 (LBBB) in addition to biventricular and RV-only pacing configurations. LV-only pacing provided significant increases in intra-electrode area variation in every configuration compared to biventricular pacing configurations. LV-only pacing from electrodes 2-3 provided improved intra-electrode area variation compared to RV-only pacing (two-tailed T-test, P=0.0006).

C. Effect of Heart Rate on Intra-electrode Area Variation.

Figure 9:
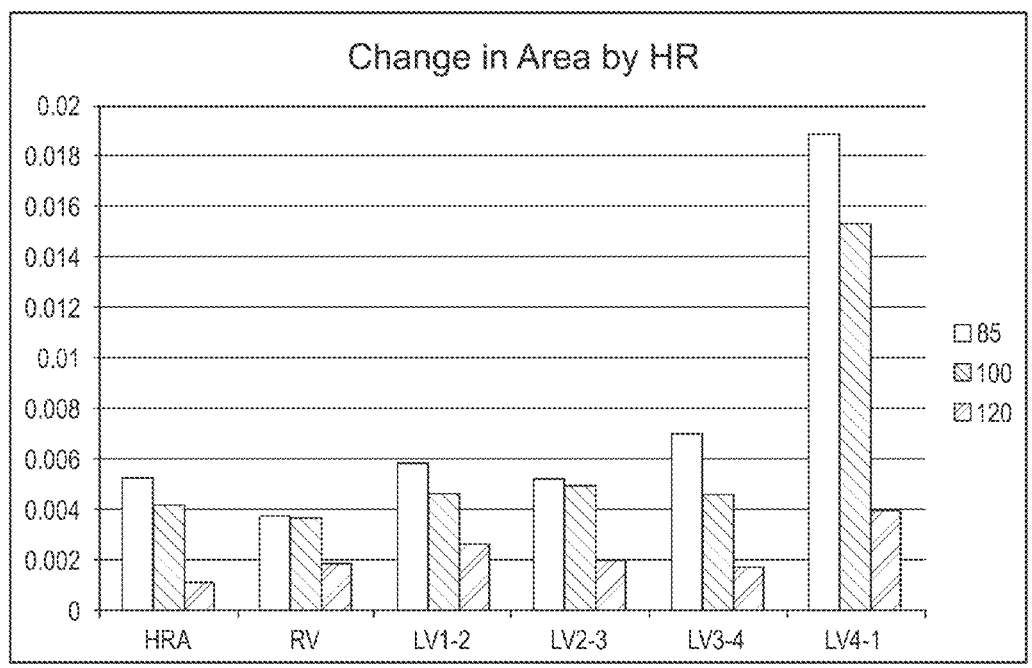
FIG. 9 is a graph showing the comparison of intra-electrode area variation by pacing rate in accordance with one embodiment of the present disclosure.

Extensive prior work has demonstrated that increases in pacing rate are accompanied by decreases in stroke volume to maintain a constant cardiac output. To determine if intra-electrode area variation measurements were capable of detecting changes in stroke volume that accompany changes in cardiac physiology, intra-electrode area variation was tested at various pacing rates of 85, 100, and 120 BPM in patient 3 (shown in FIG. 9). FIG. 9 is a graph showing the comparison of intra-electrode area variation by pacing rate in accordance with one embodiment of the present disclosure. As pacing rate increased, intra-electrode area variation decreased in all pacing configurations (P<0.0001 for all pacing configurations).

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flow chart illustrations and/or block diagrams of methods, apparatus (systems), and computer program products according to embodiments of the subject matter. It will be understood that each block of the flow chart illustrations and/or block diagrams, and combinations of blocks in the flow chart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flow chart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flow chart and/or block diagram block or blocks.

The flow chart and block diagrams in the Figures illustrate the architecture, functionality, and operation of possible implementations of systems, methods, and computer program products according to various embodiments of the present subject matter. In this regard, each block in the flow chart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow chart illustration, and combinations of blocks in the block diagrams and/or flow chart illustration, can be implemented by special purpose hardware-based systems that perform the specified functions or acts or carry out combinations of special purpose hardware and computer instructions.

Any patents or publications mentioned in this specification are indicative of the levels of those skilled in the art to which the present subject matter pertains. These patents and publications are herein incorporated by reference to the same extent as if each individual publication was specifically and individually indicated to be incorporated by reference.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. A method for cardiac resynchronization therapy (CRT), the method comprising:
receiving, during at least two time periods of a cardiac cycle, electrical signals communicated by at least two of a plurality of electrodes of a CRT device positioned one or more of on a surface of a body, within a thorax of the body, a heart of the body, a surrounding venous structure of the body, and a surrounding subcutaneous structure of the body;
calculating, based on the received electrical signals, spacing between the at least two of the electrodes during the at least two time periods of the cardiac cycle, wherein calculating the spacing comprises:
providing a coordinate model having dimensions corresponding to a major axis and a minor of the heart;
determining a maximum position value and a minimum position value of the at least two of the electrodes within the coordinate model; and
calculating the spacing based on the difference between the maximum position value and the minimum position value; and
controlling output of the CRT device to the electrodes based on the calculated spacing between the at least two of the electrodes.

2. The method of claim 1, wherein the CRT device is an implantable CRT device.

3. The method of claim 1, further comprising positioning the electrodes at the one or more of on the surface of a body, within the thorax of the body, the heart of the body, the surrounding venous structure of the body, and the surrounding subcutaneous structure of the body.

4. The method of claim 1, wherein calculating the spacing comprises calculating, based on the received electrical signals, one of a distance, area, and volume between the at least two of the electrodes during the at least two time periods of the cardiac cycle.

5. The method of claim 1, wherein the plurality of electrodes include at least one reference electrode positioned posterior to a left ventricle and at least one reference electrode positioned anterior of a right ventricle.

6. The method of claim 1, wherein the plurality of electrodes include one or more pacing electrodes positioned in at least one location selected from the group consisting of: one of the interventricular septum the apex of the right ventricle; one or the posterior and lateral coronary sinus branch of the coronary sinus; the lateral or anterior coronary sinus branch of the coronary sinus; the endocardial cavity of the left ventricle; the epicardial surface of the left ventricle.

7. The method of claim 1, further comprising providing images of the heart.

8. The method of claim 7, wherein the images of the heart are three-dimensional images of the heart.

9. The method of claim 7, wherein the images are acquired one of pre-procedural and post-procedural.

10. The method of claim 1, wherein controlling output of the CRT device comprises one of optimizing CRT therapy and modifying a pacing rate of the heart based on the calculated spacing between the at least two of the electrodes.

11. The method of claim 1, further comprising using the calculated spacing for monitoring patient condition.

12. A cardiac resynchronization therapy (CRT) system comprising:
a plurality of electrodes including at least two electrodes configured to be positioned on one or more of on a surface of a body, within a thorax of the body, a heart of the body, a surrounding venous structure of the body, and a surrounding subcutaneous structure of the body; and
a CRT device configured to:
receive, during at least two time periods of a cardiac cycle, electrical signals communicated by the at least two of a plurality of electrodes;
calculate, based on the received electrical signals, spacing between the at least two of the electrodes during the at least two time periods of the cardiac cycle, wherein calculating the spacing comprises:
providing a coordinate model having dimensions corresponding to a major axis and a minor of the heart;
determining a maximum position value and a minimum position value of the at least two of the electrodes within the coordinate model; and
calculating the spacing based on the difference between the maximum position value and the minimum position value; and
control output of electrical signals to the electrodes based on the calculated spacing between the at least two of the electrodes.

13. The CRT system of claim 12, wherein the CRT device is an implantable CRT device.

14. The CRT system of claim 12, wherein the CRT device is configured to calculate, based on the received electrical signals, one of a distance, area, and volume between the at least two of the electrodes during the at least two time periods of the cardiac cycle.

15. The CRT system of claim 12, wherein the plurality of electrodes include at least one reference electrode configured to be positioned posterior to a left ventricle and at least one reference electrode positioned anterior of a right ventricle.

16. The CRT system of claim 12, wherein the plurality of electrodes include one or more pacing electrodes configured to be positioned in at least one location selected from the group consisting of: one of the interventricular septum the apex of the right ventricle; one or the posterior and lateral coronary sinus branch of the coronary sinus; the lateral or anterior coronary sinus branch of the coronary sinus; the endocardial cavity of the left ventricle; the epicardial surface of the left ventricle.

17. The CRT system of claim 12, wherein the CRT system is configured to provide images of the heart.

18. The CRT system of claim 17, wherein the images of the heart are three-dimensional images of the heart.

19. The CRT system of claim 17, wherein the images are acquired one of pre-procedural and post-procedural.

20. The CRT system of claim 12, wherein the CRT device is configured to one of optimize CRT therapy and modify a pacing rate of the heart based on the calculated spacing between the at least two of the electrodes.

21. The CRT system of claim 12, wherein the CRT device is configured to use the calculated spacing for monitoring patient condition.

* * * * *